United States Patent [19]

Bhuchar et al.

[11] 4,006,062
[45] Feb. 1, 1977

[54] STILL EXTRACTOR WITH NOVEL STOPCOCK MEANS

[75] Inventors: Vishwa Mitra Bhuchar; Arun Kumar Agrawal; Franz Kiss; Jayanti Prasad Vasisht; Dharam Parkash; Oudh Narain Lal Srivastava, all of Delhi, India

[73] Assignee: Council of Scientific and Industrial Research, New Delhi, India

[22] Filed: Jan. 9, 1975

[21] Appl. No.: 539,845

[52] U.S. Cl. .................. 202/169; 23/272.6 S; 202/170; 203/DIG. 2; 251/309; 23/292
[51] Int. Cl.² .................. B01D 3/34; B01D 11/04
[58] Field of Search .................. 202/170, 168, 169; 203/DIG. 2; 23/272.6 S, 292; 137/625.41, 625.47; 251/309

[56] References Cited

UNITED STATES PATENTS

| | | | |
|---|---|---|---|
| 440,963 | 11/1890 | Pinagel | 202/169 |
| 859,264 | 7/1907 | Travis | 137/625.41 |
| 2,095,056 | 10/1937 | Clough | 202/168 |
| 2,991,804 | 7/1961 | Merkle | 137/625.47 |
| 3,098,506 | 7/1963 | Spragens | 137/625.47 |
| 3,108,614 | 10/1963 | Navara | 137/625.47 |

FOREIGN PATENTS OR APPLICATIONS

| | | | |
|---|---|---|---|
| 1,057,572 | 5/1959 | Germany | 23/272.6 S |
| 858,155 | 7/1949 | Germany | 23/272.6 S |
| 504,049 | 12/1954 | Italy | 23/272.6 S |

*Primary Examiner*—Frank W. Lutter
*Assistant Examiner*—Frank Sever

[57] ABSTRACT

Extraction container for solvent extraction of materials, having vapor inlet and outlet tubes, a condenser fitted on the extraction container and a stopcock fitted on the inlet tube causing distributing solvent vapors in desired proportions between those led to the said condenser and those led into the said container and also fitted with an improved syphon for discharging of extract from the container.

7 Claims, 17 Drawing Figures

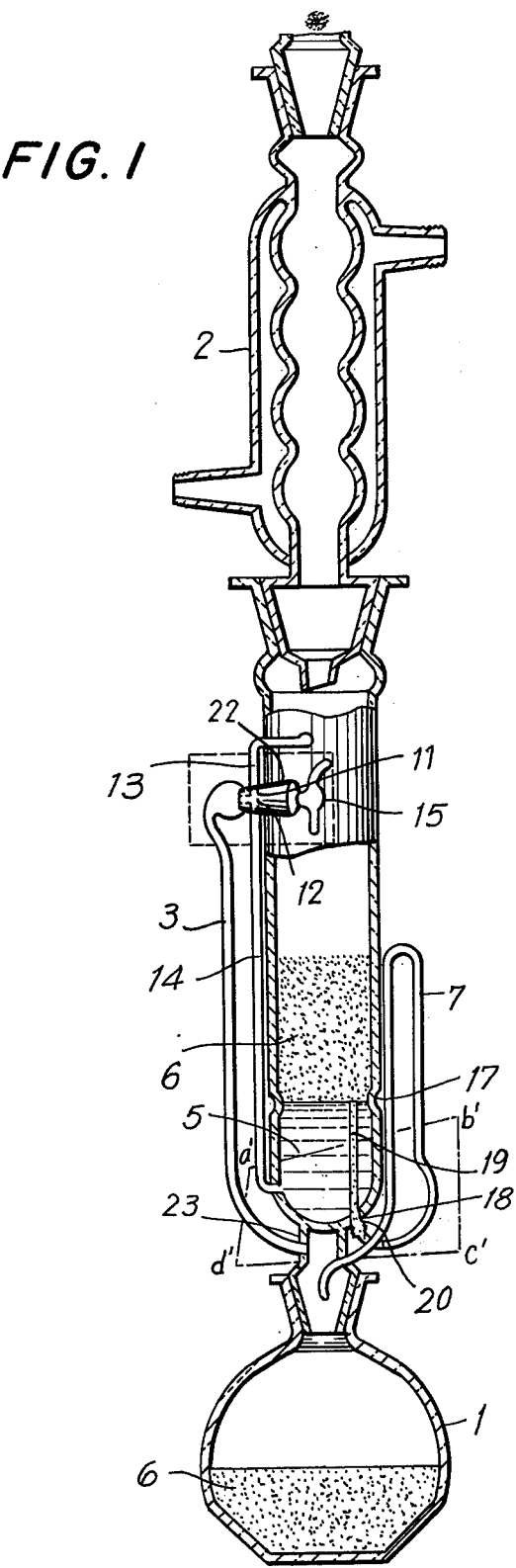
FIG. I
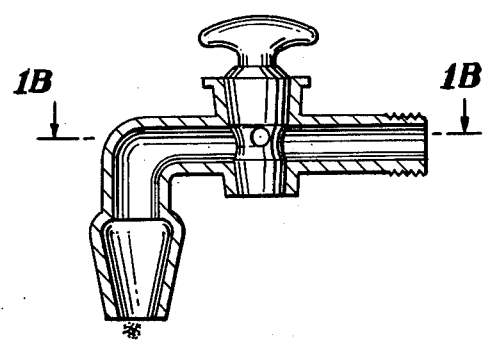
FIG. IA
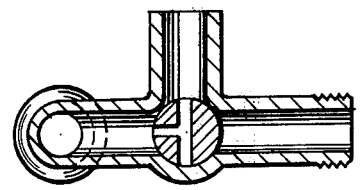
FIG. IB

STILL EXTRACTOR WITH NOVEL STOPCOCK MEANS

This invention relates to a Solvent Extractor in which some new features have been introduced and other known features of the conventional apparatuses have been utilized.

A conventional apparatus consists of the following parts :— A distillation flask, a reflux condenser, and an extraction container fitted between the distillation flask and the reflux condenser. The extraction container bears a vapor tube for conveying vapors from the distillation flask to the reflux condenser, and a siphoning system for conveying the extract from the extractor to the distillation flask. The said known conventional apparatus operates as follows:

The solvent is placed in the distillation flask and heated, the vapors of the solvent are conveyed to the reflux condenser through the vapor-lead tube and the condensed solvent drips into the extraction container which contains the solid material that is macerated with the solvent; the extract formed by the dissolution of the constituent of interest with the solvent is siphoned back to the distillation flask and this cyclic process is carried on repeatedly.

The conventional apparatus as described above suffers from the following limitations:

i. that the material to be treated with the solvent should necessarily be a solid; and
ii. that the actual treatment of the material with the solvent does not take place at a temperature which is appreciably higher than the ambient temperature.

Other conventional apparatuses for liquid/liquid extractions suffer from the shortcomings:

i. while using a separating funnel, the two liquids are shaken up manually first and then separated, it is necessarily a batch separation in a single operation;
ii. some automatic apparatuses utilize means for counter current stripping, or mechanical/magnetic mixing; and
iii. essentially all these operations are carried out at a temperature not higher than the room temperature.

This invention has for its object improvements whereby the extraction can be carried out under various conditions under which it cannot be carried out by the use of the conventional known apparatuses.

With this object in view, this invention broadly consists of a process of solvent extraction of substances solutions, liquids and solids by another liquid wherein the vapors from a distillation flask are passed in controlled proportions directly into an extractor for enabling the extraction to take place at controlled temperatures higher than the temperature of the distillate from the reflux condenser.

This invention includes also an apparatus which has in combination, a distillation flask, a reflux condenser, an extraction container located between the distillation flask and the reflux condenser, the extractor carrying vapor tubes for conveying vapors from the distillation flask to the reflux condenser and into the extraction container, and carrying a siphoning system for conveying the extract from the extractor to the distillation flask, in which apparatus a means is provided whereby the vapor-inlet from the vapor tube can be conveyed into the said extraction container in desired proportions.

The said means may be a three-way stop-cock comprising a socket and a conical plug rotatably held in the barrel, the said conical plug providing an angular path between the vapor lead-in tubes from the flask and the vapor lead-out tubes either to the reflux condenser or to the container.

As an alternative, the said device may be either a conventional three way stopcock or a modified three way stopcock in which the outlet channel is oriented not symmetrically along the diameter but obliquely in relation to it.

This invention additionally includes a modified siphon system so that the same extractor can be utilized for siphoning the extract in a lighter immeriscible solvent as well as the extract in a denser immiscible solvent extracted from another solution or liquid, or the extract of a solid in any solvent. This is achieved by providing a standard joint at the end of the shorter arm of the siphon and a fitting glass arm in reverse so that the effective length of the shorter arm could be reduced in case the liquid-lighter liquid extraction is to be undertaken.

This invention will now be more particularly described with reference to the accompanying drawings, wherein:

FIG. 1 is a diagrammatic sketch of an improved apparatus according to this invention.

FIG. 1a is a sectional view of the stopcock in FIG. 1;

FIG. 1b is a sectional view taken along line 1b—1b in FIG. 1a;

Figure 2A:
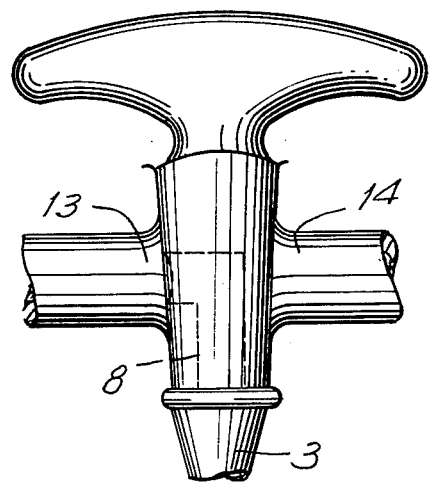
FIG. 2A is an elevational front view and shows the path provided in a two way stop cock for the passage of vapors therethrough.

In the drawings, the apparatus illustrated in FIGS. 1, 4A to 4E and 5A and 5B has for its main parts a distillation flask 1, a reflux condenser 2, a vapor lead-in tube 3 for conveying the vapors from the distillation flask 1 to the reflux condenser 2, and/or to an extraction container 4 wherein the extraction will take place by treating the material 5 with the solvent 6, and siphon system 7 for conveying the extract to the distillation flask 1.

Figure 2B:
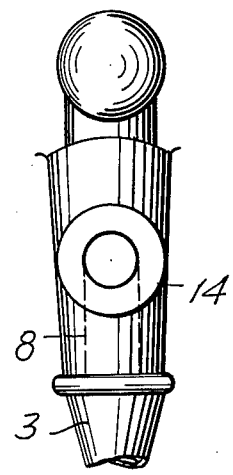
FIG. 2B is an end view of the stop cock of FIG. 2A.

Unlike a conventional known apparatus, the vapor lead-in tube 3 may be fitted with a three-way stopcock 24 (FIGS. 2A and 2B), which provides the angular path 8 to the vapor from the vapor lead-in tube 3 either to the reflux condenser 2 or to the extraction container 4, depending upon the position of the said stopcock.

Figure 3A:
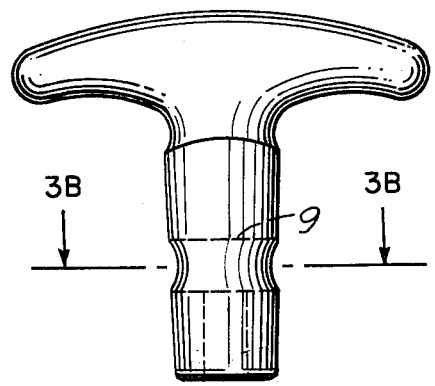
FIG. 3A shows the path for the passage of vapors as in FIG. 2A, when applied to a three way stop cock.
Figure 3B:
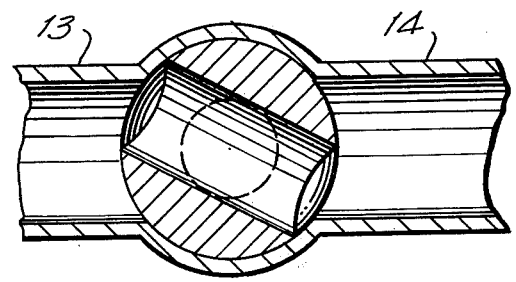
FIG. 3B is a sectional view taken along line 3B—3B in FIG. 3A.
Figure 4A:
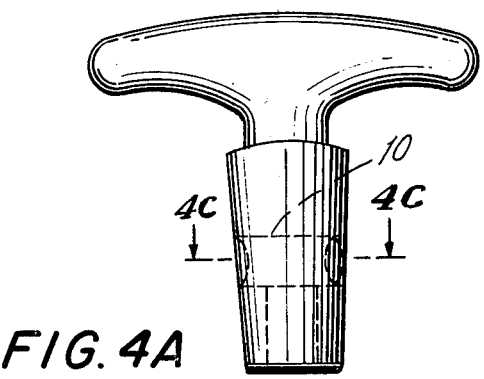
FIG. 4A is an elevational front view and shows a modified three way stop cock.
Figure 4B:
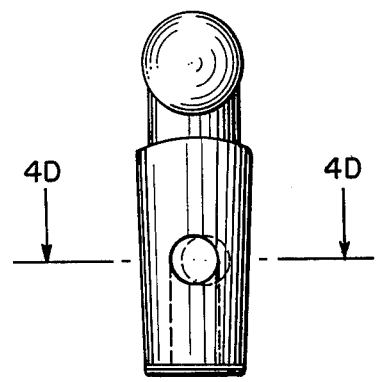
FIG. 4B is a side view of the stop cock of FIG. 4A.
Figure 4C:
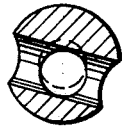
FIG. 4C is a sectional view taken along line 4C—4C in FIG. 4A.
Figure 4D:
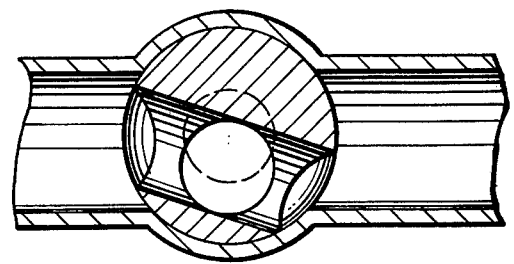
FIG. 4D is a sectional view taken along line 4D—4D in FIG. 4B and shows the relative positions of the inlet and outlet apertures provided in the stop cock of FIG. 4A.
Figure 4E:
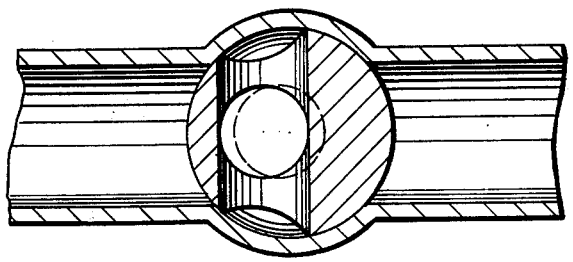
FIG. 4E is a sectional view similar to that of FIG. 4D and shows a further relative position of the inlet and outlet apertures.
Figure 5A:
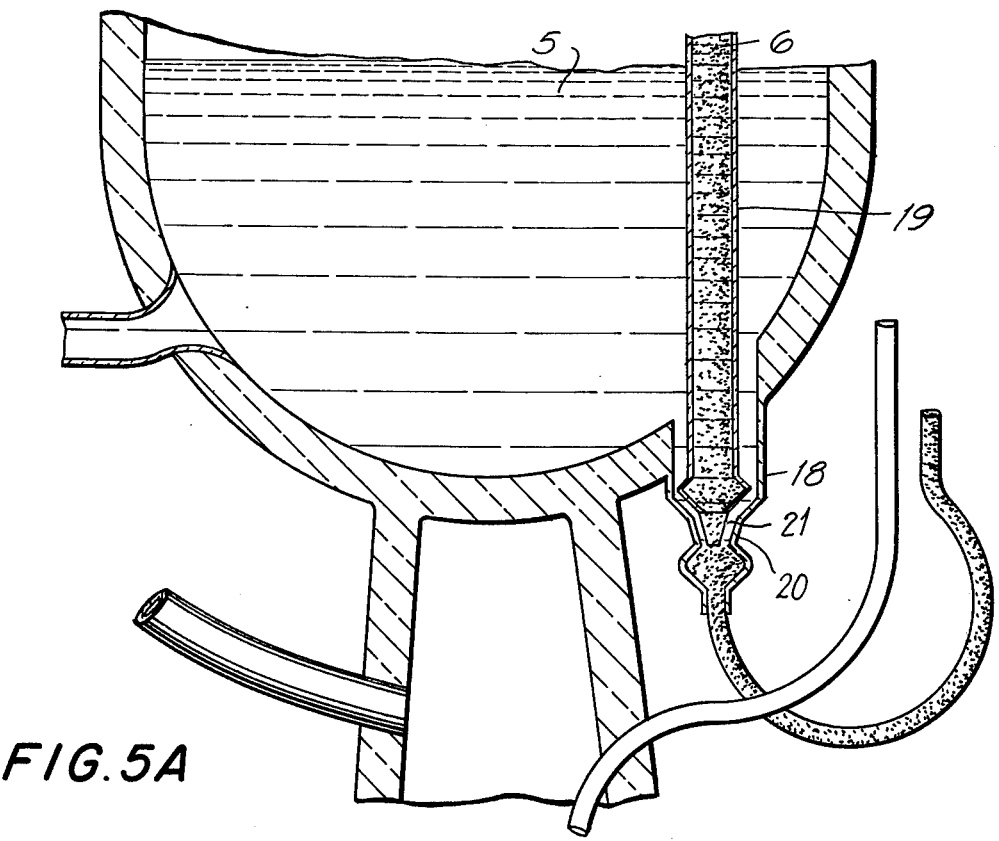
FIG. 5A is a sectional enlarged view of a siphon system provided with improved apparatus according to the present invention.
Figure 5B:
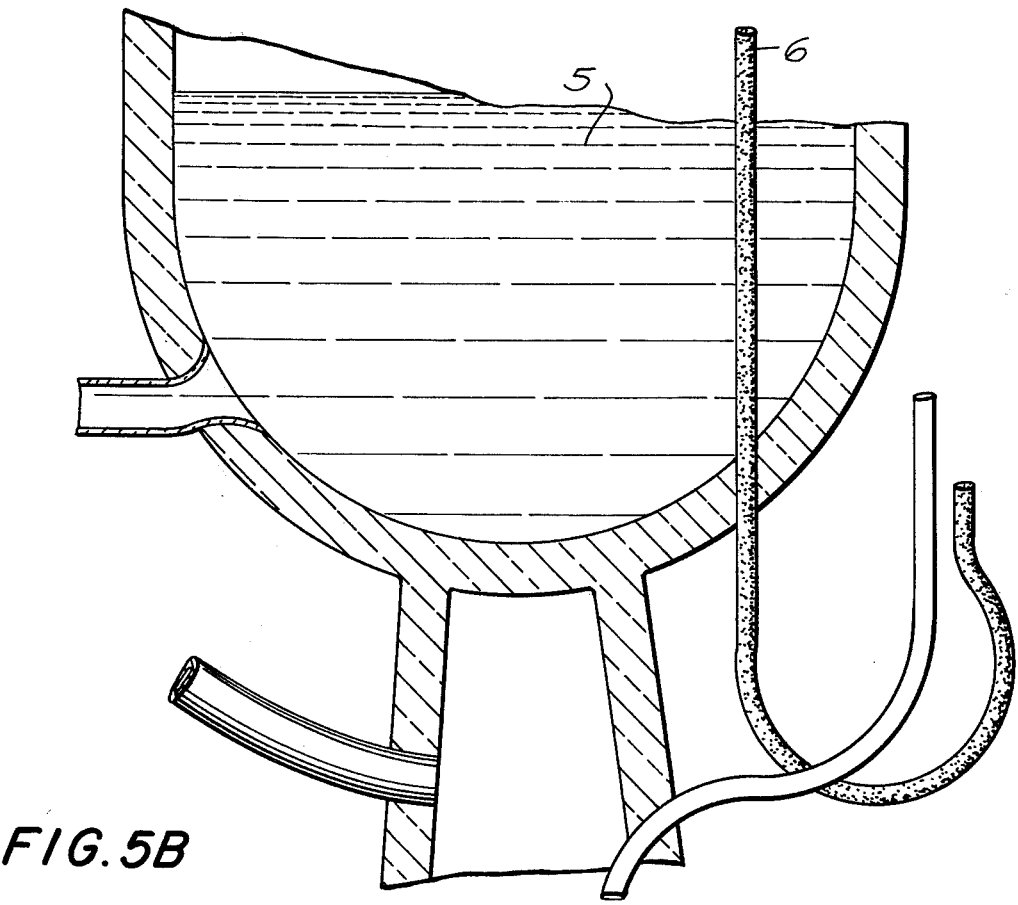
FIG. 5B is a sectional enlarged view of another embodiment of FIG. 5A.

By replacing the three-way stopcock 24 carrying two way angular channel 8 (FIGS. 2A and 2B) by the ordinary three way T-form stopcock shown in FIGS. 3A and 3B, the vapors may be passed simultaneously into the reflux condenser 2 and to the extraction container 4.

A conventional three way T-form stopcock 25 as shown in FIGS. 3A and 3B has, however, the drawback, namely, that when one of its outlets is partially open to the condenser 2, its other outlet also will be open to the same extent to the extraction container 4, (see three way path 9 in FIGS. 3A and 3B) and therefore, it will not be suitable for varying the proportions of the vapors discharged through its two outlets 13 and 14.

This drawback can be avoided by using a modified three way path 10 as shown in FIGS. 4A to 4E. In the said three way stopcock 6 (FIGS. 4A to 4E), the two outlets 11 and 12 are not diametrically opposite to each other, but are oblique in relation to the diameter 28. As a result of this obliquity, it will be possible to manipulate the stopcock suitably so that the vapors from the vapor tube 3 are distributed to the reflux condenser 2 and into the extraction container 4 in any desired proportion.

The processes described herein can be carried out under ordinary or inert atmosphere at atmospheric pressure, or at higher pressure or at reduced pressure by providing a standard joint 29 as shown in FIG. 1.

| REFERENCE NUMERAL | ELEMENT DESCRIPTION |
|---|---|
| 13 | The vapors-lead-out-tube directed towards condensor 2 |
| 14 | The vapor-lead-tube directing the vapors into the liquid or solution contained in the container 4 |
| 15 | The plug of three way stopcock 24, 25 or 26 |
| 15A | The plug of the proportionating 3-way stopcock 26 |
| 16 | The fritted glass disc to hold a pasty material meant for extraction |
| 17 | The circumferential depression |
| 18 | The end cup of standard joint (female) 20 at the bottom of extraction container 4 |
| 19 | An extension of the siphon inside the container, when extraction by a lighter solvent is performed |
| 20 | A standard female joint |
| 21 | The male standard joint to quickfit the female joint 20 |
| 22 | The socket of the three-way stopcock |
| 23 | The extension tube of the extraction container 4 with a standard male joint to fit into the standard female joint at the mouth of the distillation flask 1 |
| 24 | Three-way stopcock with 2-way angular channel 8 |
| 25 | The conventional three-way stopcock |
| 26 | Proportionating three-way stopcock |
| 27 | Oblique direction of channel 10 to the dia 28 of plug 15A |
| 28 | Diameter of plug 15A at the level of vapor-outlets 13 & 14 |
| 29 | Standard joint with 3-way stopcock |
| 30 | 3-way T-form stopcock for extraction in vacuum or under pressure |
| 31 | solvent vapors |
| 32 | extraction unit |
| 33 | connecting means. |

CONSTRUCTION OF AN EXTRACTOR OF A 100 CC NOMINAL CAPACITY

Step No. 1. Make a standard female ground glass joint at one end of a length of a 40 mm dia. glass tube (extraction container 4).

2. Make a standard ground glass at one end of a length of a 20 mm dia. glass tube 23.

3. Make a standard female 20 with a cup 18, and fuse to 4 mm diameter tubes. Make a standard B7 male joint 21.

4. Make standard socket 22 and solid or hollow plug 15 for a special three way stopcock (FIGS. 4A to 4E).
   a. socket 22 — Two openings (8 mm dia.) are made into the body of the socket 22 at right angle to the main passage and an 8 mm tube is fused to each of the openings at 180°. This is then rough ground.
   b. plug 15 — Taper a glass rod to the size of a male part of size. Make the three way holes 3, 11 and 12 as per drawing (FIGS. 4A and 4C) with the help of a molybdenum rod of the size of 5 mm.
   Alternatively the three-way hole 3, 11 and 12 could be drilled into the plug 15 with a diamond drill at a milling machine.
   Join the glass tube handle with a pointer properly aligned to one of the side holes. Grind the male and the female parts together to vacuum tight fineness.

5. Fuse 4 mm glass tube with a slant-cut-end to the inside of the tube 23 attached to male joint.

6. Into the tube 23, fuse 8 mm tube opposite to the 4 mm siphon tube 7.
   As an alternative, the 8 mm vapor-lead-in tube 3 could be fused in an alignment on the same side as the siphon tube 7.

7. At the proper length fuse the open end of the tube 23 attached to male joint with the closed end of the extraction container tube 4.

8. Make the circumferential depression 17 on the extraction container tube, 40 mm from its closed end 24. The capacity of the extraction container up to the depression 17 is 50 cc.

9. At the bottom of the extraction container 4 fuse the female of the standard joint 20 in the same alignment as the siphon tube 7 had already been fused in the tube 23. Or this may be fused at any convenient position beneath the closed end of the extraction container.
   In case of the samll capacity extractors, say 200 cc nominal capacity and less, fuse the standard female joint 20 with cup 16 in the center of the bottom of 4. The joint carries a small 4 mm tube which may be fused in the side of the tube 23 attached to and further to the siphon tube 7. This operation is done between steps 6 and 7.

10. Join up the free ends of the siphon tube to form a complete siphon tube 7 as shown in FIG. 1.
   As an alternative to the one described above, the two arms of the siphon tube could be concentric.

11. Anneal the extractor made as described above at about 500° C over a reducing flame of the burner for about 15 minutes, or in an annealing oven at about 550° C.

12. Fix up the three way stopcock socket 22 to the vapour lead tube 13, 14 and 3 as shown in FIG. 1.

13. Make a standard male joint 21 with a 5 mm diameter tube 19: fine grind it against female joint 20. The length of tube 19 could be adjusted as required.

13. Insert the plug 15 or 15A into the socket 22, and secure it with a thread or rubber band.

14. Fabricate a 500 cc F.B. flask with a female joint and a condenser with male joint. Fit them together as shown in FIG. 1 on an iron stand with a clamp.

The same mode of construction as described above is followed for constructing extractors of other capacities by changing the dimensions of tubes and size of the standards joint as suitable.

The nominal capacity of an extractor is the volume up to the level of the top of the siphon and is twice the capacity of the tubes. It can accommodate equal volumes of the solution and the extractant. The length of the extractor tube from base to the top of the cone may vary 3–4 times the length.

MANIPULATION

The following examples illustrate how the said apparatus may be used for extraction in various ways:

The three modules for example, a boiling flask 1 containing the solvent, reflux condenser 2 and the extraction container 4 between them are secured by a clamp borne on an iron stand. A heater is placed under the flask.

A. i. EXTRACTION BY LIQUIDS OF A SOLID

The solid is wrapped in a filter paper, a piece of cotton cloth or an extraction thimble, and is placed in the extraction container 4. The solvent in the boiling flask is heated to vaporize. The plug 15 of the stopcock is closed to vapor lead-out tube 14 and opened fully to the vapor-lead-out 13, thereby leading the vapors to the condenser 2 and to get condensed. The condensed solvent drips into the extraction container 4, and disolves away the constituent of interest. The vaporization and extraction continues till the extractant fills the extraction container 4 to the level of the siphon top 7. The said extractant enriched with the said constituent, siphons off to the boiling flask 1. The operation described above then repeats. In this way repeated extraction of a constituent from a solid by a recycled fresh solvent can be performed.

EXAMPLE 1

100 g of the coffee seeds, which had been roasted, ground and sieved to 30 mesh size, were taken in a clean cambric cloth bag. This powder was extracted with alcohol repeatedly by recycling it as described above. The extract filtered, concentrated, treated with 100 g of magnesium oxide and dried. Hot water solubles were filtered out, concentrated and treated with dilute (1:9) sulfuric acid. From the aqueous solution the caffein was extracted with chloroform as described under B(i) below. The chloroform was evaporated off and the caffein was crystallized from hot water solution; yellow solid of m.p. 210° C, yield 1.3%.

ii. EXTRACTION OF SOLID, E.G., RICE HUSK BY A LIQUID, E.G., CYCLOHEXANE, AT HIGHER TEMPERATURE

The extraction is carried out as in A(i) but with the difference that the vapors 31 are allowed to pass through the liquid collected in extraction container 4 so that they heat the liquid as well as stir it. The temperature of extraction can be controlled by adjusting the plug 15A so that partially the vapors pass to the vapor-lead-out tube 13, condense and drip back, and partially they pass through the vapors-lead-out-tube 14 and thence through the liquid in extraction container 4 as hot vapors to heat it and stir it up.

EXAMPLE 2

50 g of rice husk were filled in the extraction container and extracted repeatedly with cyclohexane (b.p. 81°) in the extractor at a temperature of 75°–79° by recycling it as described above. The extractables were freed of the solvent by vaporation and drying. The extractables were found to be 0.50 percent.

EXAMPLE 3

400 g green coffee seeds were macerated and extracted (4 times) with water in a 800 cc multipurpose extraction container as described above. The aqueous extract was concentrated to 200–250 cc and treated with 100 cc (1:9) sulfuric acid. From the aqueous extract, the caffein was extracted with trichloroethylene at a temperature of 75°–80° C as described under B(i) below. The trico was evaporated off, and the caffein was crystallized from hot water, yield 0.9%. Recrystallized from trichloroethylene, whitish solid of m.p. 208° C.

iii. EXTRACTION OF RATHER STICKY SOLID BY LIQUID AS IN (i) AND (ii) ABOVE.

The sticky solid is spread over a fritted disc 16 bearing holes of 0.1 mm diameter all over its surface, and itself fitting sluggishly over the depressed circumference 17. Extraction was then carried out in the usual way.

B. i. EXTRACTION OF A SOLUTE FROM A SOLUTION BY A HEAVIER IMMISCIBLE SOLVENT

The solution is taken into the extraction container 4 and the vapors 31 are allowed to pass through it through the vapors-lead-tube 3. These vapors serve the dual purpose of heating and stirring the liquid. If the extraction is to be carried out at a lower temperature, the vapors are partially directed to the vapor-lead-out-tube 13 by adjusting the position of the plug 15A.

Figure 7:
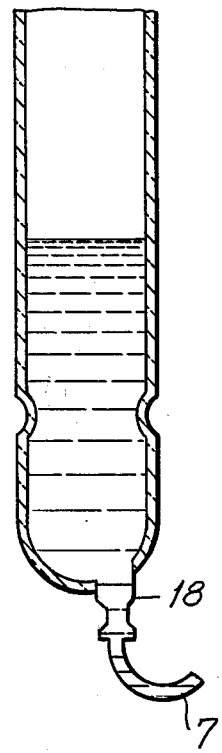
FIG. 7 is a sketch corresponding to FIG. 6, when the treated liquid is lighter than the solvent.
Figure 8:
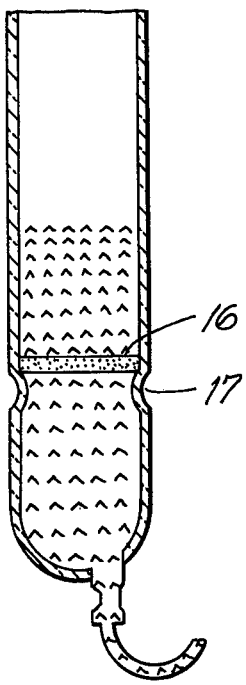
FIG. 8 shows the extractor fitted with a fitted glass disc on the depression for extraction of a paste like substance.

The operation is continued till the extraction container is nearly filled to a depth a little before the siphoning takes place. The vapors are slowly turned towards the vapor-lead-out-tube 13 in the manner that the pressure is sufficient to hold back the liquid's entry into the siphon tube 7 (FIG. 7). This position is retained for a short while till the partition has taken place above the siphon end 18. The vapors are then directed entirely to the vapour-lead-out-tube 13. The condensed liquid drips back from the condenser 2 while the mixed up liquids separate. The siphoning is now allowed to take place till partition surface of liquids reaches 18. The siphoning is broken off quickly by turning the plug 15 to the closed position, FIG. 4E with the result that the back pressure of the vapor in the siphon breaks off the siphoning. The stopcock is opened to 13. The process is repeated many times in the sequence described above.

If necessitated in the course of an extraction processing, the siphoning can be broken at any moment during siphoning by the turn of the plug 15A to closed position in order to create a back pressure into the siphon tube 7 as stated above.

ii. The extraction of a solution by a heavier solvent can be carried out at any temperature between above room temperature to boiling point as described in A(i) and A(ii) Examples (See Examples 1 and 3 under A; extraction of aqueous caffein solution by chloroform); and

EXAMPLE 4

Extraction of Iodine with carbon tetrachloride from aqueous Iodine solution.

Repeated extraction at 70° of iodine was carried out each time by 50 cc of carbon tetrachloride, from 50 cc of aqueous solution of 0.002M iodine containing 0.1M potassium iodide. The extraction was carried out at a temperature of 70° C obtained by passing of vapors partially through the vapor-lead-out-tube 14. Each time the extract was induced to siphon off when 50 ccs of this had been collected. The siphoning was broken off as described by closing the stopcock 15 and creating a back pressure in the siphon 7. A few cc of the extract was each time held back in the extraction container and pipetted out to determine its absorbance. The progress of extraction of iodine into the carbon tetrachloride was noted from its absorbance at room temperature after drying the extract with dry sodium sulfate.

The absorbance was plotted against the volume of extractant (no. of extractions × 50 cc) on a semilogarithmic paper. The curve comprised of two straight arms of different gradients. The low gradient of the later part of extraction pointed to the formation of a more stable complex of iodine with higher proportion of potassium iodide.

The distribution factor $k$ under the conditions mentioned for each arm was calculated from the formula $$K = \frac{0.693 \times w}{v}$$

wherein $w$ is the original volume of the solution and $v$ the half extraction volume. The values for the two arms of the curve were found to be: $k = 1.08$ and $0.165m$ & $V_{0.5EX} = 32$ and $210$ cc when 50 cc of the original aqueous iodine solution was taken for extraction. ($V_{0.5EX}$ is the half extraction volume. It denotes the volume of the extractant that would reduce the amount of the constituent of interest in the solution to half its original value.) It may be noted that in the iodine solution the molar ratios of iodine to potassium iodide were 1:50 and 1:1000 respectively for extractions corresponding to first and the second arms of the curve. The behavior conforms to the one described in an earlier work of Bewick et al. in Analytical Chemistry, 14(1948)740.

EXAMPLE 5

Extraction of aqueous phenol solution by chloroform

Repeated extraction at 55° C of 1% aqueous solution of phenol was carried out each time by 50 cc of chloroform. The extraction was carried at a temperature of 55° C obtained by passing the chloroform vapors partially through vapor lead-out-tube 14 and partially through vapor-lead-out tube 13. Each time siphoning was induced to take place, when 50 cc of the extract had collected, in the same manner as described in example 4. 2 cc of the each sequential extract in chloroform was metered out and treated with standard 0.1M potassium bromate solution in $CO_2$ atmosphere in fairly acidic solution. After 10–15 minutes reaction in the dark, the excess of bromate solution was titrated back with 0.05N sodium thiosulfate for the iodine liberated from reaction with potassium iodide. The titer of potassium bromate for each successive 2 cc of the extract gave the measure of the progress of extraction. The titer values were plotted against volume of the extract as in example 4. This exercise gave a value of $k = 1.02$ and $V_{0.5EX} = 34$ cc for extraction of 50 cc of 1% aqueous phenol solution by chloroform.

The extraction was completed in 1¼hrs. i.e., in one fifth the time required in another extractor used by Dow Chemicals, U.S.A., as described by S.W. Tobey in Journal of Chemical Education, 49(1972)141.

C. i. EXTRACTION OF SOLUTE FROM A SOLUTION BY A LIGHTER IMMISCIBLE SOLVENT

Figure 6:
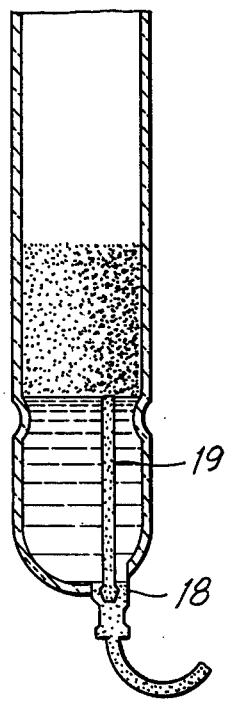
FIG. 6 shows the positions of the treated liquid and the solvent in the extractor when the treated liquid is heavier than the solvent used for extraction.

The solution is taken into the extraction container 4. The siphon arm 19 is inserted in the opening of the siphon at 18 and the height of 19 is adjusted up to the surface of the solution, because 19 could be collapsible; or else the surface of liquid could be adjusted to the tip of the siphon arm 19 (FIG. 6). The vapor of the lighter solvent from the boiling flask 1 are led into the solution through the vapor-lead tube 14 as described in B(i) above, till a little before the siphoning. Any solution that may have entered the siphon is thrown off by momentary closing of the stopcock. The solvent is held back from entering the siphon arm 19 with the help of the turn of the plug 15 and the consequential back pressure of the vapor till the liquids have separated out. The plug 15 is then turned on to the vapor-lead-out-tube 13 so that the vapors are entirely directed to the condenser 2. Then the siphoning takes place only up to the level of partition, i.e., the tip of the siphon arm 19. After the siphoning off the lighter liquid containing the solute, the operation continues repeating. ii. The extraction of solute from a solution by an immiscible lighter solvent can be carried out at any temperature from above room temperature to boiling point as described in A(i) and (ii).

EXAMPLE 6

Extraction of Iodine with benzene from aqueous iodine solution

Repeated extraction at 67° C of iodine, each time by 50 cc of benzene, a lighter solvent (red - violet solution, from 50 cc of aqueous solution of 0.002M iodine containing 0.1M potassium iodide was carried out in the manner described under manipulation C(ii). The progress of extraction of iodine into the benzene was noted from the absorbance at room temperature.

The absorbance of successive extracts was plotted against the volume of the extract on a semi-logarithmic paper as described in example 4. The curve showed a straight line of a gradient nearly parallel to the first arm of carbon tetrachloride – extraction of iodine curve (example 4).

Distribution factor $k$ of iodine in benzene from aqueous potassium iodide solution under the conditions mentioned was calculated to be 1.06, and half extraction volume $V_{0.5EX} = 33$ cc for 50 cc of aqueous 0.002M iodine solution in 0.1M potassium iodide.

D. DETERMINATION OF DISTRIBUTION COEFFICIENT OF A SOLUTION BETWEEN TWO IMMISCIBLE SOLVENTS

The distribution extraction is carried out by denser or lighter solvent as described under (B) or (C); and the distribution factors determined as described in examples 4, 5 and 6 are given in Table 1.

Table 1

| Description of the solution being extracted | Conditions of extraction | Distribution factor 'k' | | Half Extn. volume $V_{0.5EX}$ | Refer to example |
|---|---|---|---|---|---|
| 0.002M iodine in 0.1M potassium iodide, aq. | Temp. of extn. 70°; each extn. was done by 50 cc of carbon tetrachloride | (i) | 1.08 | 32 cc | 4 |
| | | (ii) | 0.17 | 210 | 4 |
| 0.0965M phenol solution in water (50 cc) | Temp. of extn. 55°; each extn. was done by 50 cc of chloroform | | 1.02 | 34 | 5 |
| 0.002M iodine in 0.1M potassium iodide, aq. | Temp of extn. 67°; each extn. was done by 50 cc of benzene | | 1.06 | 33 | 6 |

Advantages related to Table 1
(i)
It is a composite and easily workable apparatus which can be used for extraction by solvents, both heavier or lighter, of a solute of interest from its solution or from another solid.
(ii)
it can be assembled on a laboratory bench and secured by an iron clamp and stand. No special frame is necessary.
(iii)
It is simple to operate, can be used for batch extraction, but repeatedly with recycled fresh solvents.

ADVANTAGES RELATED TO TABLE 1 i. It is a composite and easily workable apparatus which can be used for extraction by solvents, both heavier or lighter, of a solute of interest from its solution or from another solid.

ii. it can be assembled on a laboratory bench and secured by an iron clamp and stand. No special frame is necessary.

iii. It is simple to operate, can be used for batch extraction, but repeatedly with recycled fresh solvents.

iv. The extraction can be carried out at any temperature from above room temperature to boiling point of the solvent at reduced, atmospheric or increased pressure in a desired atmosphere.

v. The mixing and extraction can be facilitated without providing any separate stirrer. The passing vapor performs this function.

vi. The apparatus can be used for preparative purification/analytical work by simple changing the diameter of the extraction chamber.

vii. The apparatus can also be used for determinations of academic interest for example the determination of distribution co-efficient, half extraction volume; and purification etc.

viii. The extraction with this apparatus is cheaper and more efficient.

ix. The apparatus can be easily assembled, dismantled, cleaned, stored and transported.

It is to be understood that the processes described herein can be carried out at atmospheric pressure, or at higher pressure, or at reduced pressure or under any inert or reactive atmosphere.

What we claim is:

1. A solvent extractor comprising a distillation flask, an extraction unit connected to said distillation flask and a condenser, said extraction unit comprising:
    a container for holding a substance for treatment with a solvent,
    a vapor inlet tube through which the vapor of a solvent may be introduced into said container,
    vapor outlet tubes fitted on the said container so that said vapor may be conveyed to a reflux condenser,
    connecting means to connect the vapor-inlet tube and the vapor outlet tubes, and
    siphon means whereby the extract collected in the container may be discharged from said container to the distillation flask, said siphon means having a bent tube formed of two legs comprising a shorter leg having the outlet for the extract from the container and a longer leg having the extract discharging extremity into the distillation flask;
    said connecting means comprising:
    a three-way stopcock between said inlet and said outlet tubes, said stopcock further comprising a plug having an inlet channel and an outlet channel arranged such that the longitudinal axis of said outlet channel is normal to, but displaced from the longitudinal axis of said plug, the vapor conveyed through the said inlet tube being distributable between said reflux condenser and said container;

the siphoning of the extract being broken off by closing said stopcock, thereby enabling the original substance to be retained in the container.

2. An extractor as claimed in claim 1 wherein said stopcock is a three-way stopcock having in the plug an angular path to the vapor passing therethrough.

3. An extractor as claimed in claim 1 wherein said stopcock comprises a conventional three-way stopcock.

4. An extractor as claimed in the preceding claim 1 including a standard joint at the outlet of the shorter leg of the siphon at the bottom of the container, and a quick-fit, removable and adjustable extension arm fitted to the shorter leg in reverse whereby the effective length of the shorter leg is reduced, thereby enabling the extractor useable for siphoning the extract of a solution by a lighter non-miscible solvent.

5. An extractor as claimed in claim 1 wherein said vapor may be conveyed further to said substance introduced in said container.

6. A solvent extractor comprising a distillation flask, an extraction unit connected to said distillation flask, and a condenser, said extraction unit comprising:

an extraction container for holding a substance for treatment with a solvent, a vapor-inlet tube through which the vapor of a solvent may be introduced into said container from a source such as from a distillation flask, vapor-outlet tubes on said container so that said vapor may be conveyed to the condenser, connecting means to connect the vapor-inlet tube and the vapor-outlet tubes, and siphon means so that the extract collected in the container may be discharged from said container to the distillation flask, said siphon means comprising a bent tube formed of two legs, with a shorter leg having the outlet for the extract from the container and a longer leg having the extract discharging extremity into the distillation flask, said connecting means comprising a proportionating three-way stopcock comprising further:

a. a socket having an inlet and two outlets, and b. a fitting plug having an inlet channel and an outlet channel arranged such that the longitudinal axis of said outlet channel is normal to, but displaced from the longitudinal axis of said plug, c. the socket and the plug comprising said three-way stopcock between said inlet and outlet tubes so that the solvent vapors from the distillation flask are enabled to be proportionated between those led to the condenser and those led into the substance contained in the container whereby the temperature of extraction can be controlled, immiscible phases can be allowed to separate, the siphoning of the extract can take place, the siphoning of the extract can be broken at will.

7. An extractor as claimed in claim 6 wherein said vapor may be conveyed further to the substance introduced in said container.

* * * * *